(12) United States Patent
Göllner et al.

(10) Patent No.: US 9,744,286 B2
(45) Date of Patent: Aug. 29, 2017

(54) CONNECTION SYSTEM FOR CREATING A CONNECTION CHANNEL FOR BODILY FLUIDS

(75) Inventors: Manfred Göllner, Berlin (DE); Uwe Samlenski, Berlin (DE)

(73) Assignee: Berlin Heart GmbH, Berlin (DE)

( * ) Notice: Subject to any disclaimer, the term of this patent is extended or adjusted under 35 U.S.C. 154(b) by 232 days.

(21) Appl. No.: 14/117,425

(22) PCT Filed: May 15, 2012

(86) PCT No.: PCT/EP2012/002149
§ 371 (c)(1),
(2), (4) Date: Jun. 5, 2014

(87) PCT Pub. No.: WO2012/156100
PCT Pub. Date: Nov. 22, 2012

(65) Prior Publication Data
US 2014/0276326 A1 Sep. 18, 2014

Related U.S. Application Data

(60) Provisional application No. 61/486,435, filed on May 16, 2011.

(30) Foreign Application Priority Data

May 16, 2011 (EP) .................................. 11075089

(51) Int. Cl.
*A61M 1/36* (2006.01)
*A61M 39/10* (2006.01)
*A61M 39/12* (2006.01)
*A61M 1/10* (2006.01)
*A61M 25/00* (2006.01)

(52) U.S. Cl.
CPC ........ *A61M 1/3659* (2014.02); *A61M 1/1008* (2014.02); *A61M 1/3653* (2013.01); *A61M 39/10* (2013.01); *A61M 39/1011* (2013.01); *A61M 39/12* (2013.01); *A61M 25/0014* (2013.01); *A61M 25/0097* (2013.01)

(58) Field of Classification Search
CPC ......... A61M 1/3659; A61B 2017/1107; A61B 2017/1132
USPC .............................. 606/153; 604/533; 600/16
See application file for complete search history.

(56) References Cited

U.S. PATENT DOCUMENTS 3,683,926 A * 8/1972 Suzuki .......................... 606/154
5,868,437 A 2/1999 Teague
5,980,448 A * 11/1999 Heilman et al. ................ 600/16
(Continued)

FOREIGN PATENT DOCUMENTS

CA 2 491 148 12/2003
DE 3715911 A1 11/1988
(Continued)

*Primary Examiner* — Diane Yabut
(74) *Attorney, Agent, or Firm* — Brinks Gilson & Lione (57) ABSTRACT

A connection system for creating a vascular cannula for connection to a blood vessel includes a flexible hose element in the form of a graft, a conduit element and, disposed therebetween, a connecting element establishing fluid-tight connections, wherein a retaining element is equipped with a radially outwardly elastically beadable snap ring, which, in the connected state, can be snapped in behind a detent surface of one of the parts of the connection system.

18 Claims, 4 Drawing Sheets

(56) References Cited

U.S. PATENT DOCUMENTS

| | | | |
|---|---|---|---|
| 5,989,287 A * | 11/1999 | Yang | A61B 17/11 600/36 |
| 6,942,672 B2 | 9/2005 | Heilman et al. | |
| 2003/0078592 A1 | 4/2003 | Heilman et al. | |
| 2004/0087986 A1 * | 5/2004 | Ott | 606/153 |
| 2005/0080482 A1 * | 4/2005 | Bonsignore | 623/1.35 |
| 2005/0137614 A1 * | 6/2005 | Porter | A61B 17/11 606/153 |
| 2007/0056744 A1 * | 3/2007 | Ellington | E21B 17/02 166/380 |
| 2007/0197855 A1 * | 8/2007 | Richardson et al. | 600/16 |
| 2011/0313237 A1 * | 12/2011 | Miyakoshi et al. | 600/16 |

FOREIGN PATENT DOCUMENTS

| | | |
|---|---|---|
| DE | 10 2009 047 844 | 3/2011 |
| EP | 1 516 142 B1 | 8/2007 |
| GB | 2 407 593 | 5/2005 |
| WO | WO 2010050114 A1 * | 5/2010 |
| WO | WO 2011/039101 A1 | 4/2011 |

\* cited by examiner

CONNECTION SYSTEM FOR CREATING A CONNECTION CHANNEL FOR BODILY FLUIDS

CROSS-REFERENCE TO RELATED APPLICATIONS

This application is a 371 nationalization of PCT/EP2012/002149, which in turn claims benefit of European patent application 11075089.0 filed on May 16, 2011 and U.S. provisional application 61/486,435 filed on May 16, 2011.

BACKGROUND

The invention applies to the field of mechanical science and relates to the creation of fluid-tight connection channels that can comprise, in part, hoses, tubes, connectors and other elements that can have passages. The invention can be applied especially in the field of medical technology, inter alia, where it can be used to easily create a connection between various conduit elements and tube elements.

In operations in particular, that involve the cardiovascular system in the human body, such as surgery performed on blood vessels, it is often necessary to create new connection channels in order to convey blood. To this end, a first tubular element that is somewhat flexible but not radially expandable is often connected directly to a vessel, said tubular element also being referred to as a graft. It must then be possible to connect this first element to an advancing conduit element in the most flexible manner possible without the need to use complex tools. The connection must be tight and reliable and must not create any dead water spaces in the blood stream, in which blood could collect and coagulate.

Connection systems have already been a fundamental focus of medical technology. For example, U.S. Pat. No. 6,942,672 B2 makes known a connection system comprising a graft that can be connected to a blood vessel and, at the opposite end, to a conduit element.

Document EP 1 516 142 B1 makes known a connection system for a cannula and a tube that comprises elements that can be inserted into each other and an axial retaining device of the connection having snap-type locking bolts.

Document DE 37 15 911 C2 makes known a device for connecting a tube tip to a tube end of an extracorporal medical supply system.

Proceeding from the prior art that was mentioned, the problem addressed by the present invention is that of creating a connection system that permits the simplest possible connection of conduit elements using the simplest possible design, wherein the connection is reliably fluid-tight and various elements can be joined shortly before or during surgery using simple means.

SUMMARY

To this end, in the case of a connection system for creating a vascular cannula that comprises a flexible tube element, more particularly a radially non-expandable graft, a conduit element and a connecting element for fluid-tight connection to the tube element and to the conduit element, the connecting element axially overlaps the tube element and the conduit element, and a retaining element is equipped with a radially elastically expandable snap ring, which can be beaded radially outwardly over other parts of the retaining element, and which, in the connected state, can be snapped onto an element of the connection system.

The tube element, the conduit element and the connecting element located therebetween can be axially plug-connected and, advantageously, are each sealed by way of a radial seal. A simple plug connection is advantageous in that the tube element, the connecting element and the conduit element can be made of different materials and can be subject to different disinfection and/or storage requirements. It is advantageous to store the individual elements of the connection system separately from one another and to be able to combine them shortly before or during the operation. The individual parts can also be procured from different manufacturers. If it becomes necessary to replace one of the parts during surgery, for example, if the graft is shortened incorrectly, the remaining parts can still be used without a problem, and the part to be exchanged can be replaced individually.

The flexible tube element is designed as a graft, typically in the form of a corrugated-tube like or spiralled, hose-shaped or tubular formed body that is often made of polyester fabric or PTFE. Said hose element is often used as a replacement for a blood vessel and is typically sutured directly to the vessel or can be connected to a blood vessel or a heart wall in a fluid-tight manner by way of a flange-type device, such as a sutural ring or a similar construction.

A graft should be flexible enough to be capable of adapting to unique anatomical details and to limit the effect of forces on blood vessels. For this reason, a graft can usually be flexibly bent toward all sides. However, it can be designed, for example, such that it is practically non-expandable radially despite this flexibility. As a result, special requirements are placed on the connectability of advancing conduit elements to a graft, for instance if they are intended to be plugged into the graft. In this context, the connection technique according to the invention using the multiple-component system makes it possible to create a reliably tight, detachable connection that is likewise easy to handle during surgery and when joining the connection system.

For example, the connecting element can be made of a metal, more particularly of titanium, and is then practically non-deformable. As an advantage, the diameters of the graft and the connecting element should be matched precisely to one another. The graft can also be partially slotted on the end to permit it to be slid over a protruding collar onto the connecting element and to be affixed behind the collar on the connecting element by way of a thread binding. The conduit element can be made of polyurethane or silicone, for example, and can be elastically expandable and, therefore, can be slid onto the connecting element or inserted therein relatively easily.

The retaining element according to the invention that comprises the expandable snap ring basically has the function of establishing and securing the axial hold of the connection system. To this end, the retaining element is typically fixedly connected to an element of the connection system, and the snap ring of the retaining element can be snapped in behind a detent surface of another part of the connection system in such a way that the axial hold is established.

In addition, the diameter and the expandability of the snap ring can be designed such that, in the connected state, after having been snapped in behind the detent surface onto the element of the connection system onto which it is snapped, it also exerts a compression effect in the radial direction and therefore presses two seal elements together that perform a sealing function there by way of a radial seal. As a result, the axial hold as well as the radial sealing of the individual parts of the connection system are supported and secured.

Advantageously, the retaining element can be connected to the conduit element, in particular being joined thereto as a single piece. The conduit element can also be formed directly as a pump connection. It can be formed as a single piece with parts of the pump, for example.

In this manner, the snap ring of the retaining element can snap in behind an azimuthally circumferential web of the connecting element or the flexible hose element, for example, in order to establish the axial hold. The snap ring can also snap into a corresponding groove in an element to be connected to the conduit element, for example.

If the conduit element is made of an elastic material, for example, such as a silicone elastomer, the retaining element can be integrally formed therewith as a single piece and can be made of the same material. The retaining element can be in the form of a type of film hinge that is fastened to the outer jacket surface of the conduit element and, proceeding therefrom, forms a hose piece that coaxially encloses the conduit element and terminates in the snap ring.

The retaining element can also be described as a flange that extends around the conduit element on the outside, on which a tube piece is fastened, said tube piece extending coaxially with respect to the conduit element and terminating in the snap ring, wherein the tube piece comprises at least one weakening region in which the wall thereof is weakened in an azimuthal circumferential manner in such a way that the hose piece can be beaded there in entirety. By way of this beading, the snap ring is expanded and folded back behind other parts of the tube piece or the retaining element. In this position, the retaining element can be self-stabilizing, and so the snap ring can be preloaded before surgery, for example, and then, to establish a connection of the connection system using relatively little effort, need only be folded over toward the end of the conduit element in order to snap in behind a detent surface of a connecting partner.

The retaining element can also be connected directly to the conduit element, in particular being joined thereto as a single piece. In this case, the retaining element must be made of a different material than the connecting element to ensure that it is adequately elastically deformable. Otherwise the retaining element can also be easily joined to the connecting element using common joining techniques, for example by adhesive bonding, casting-on or similar methods. The retaining element can then be connected to the conduit element or to the flexible hose element by snapping on the snap ring accordingly.

It is also possible to equip the connecting element with a plurality of retaining elements, one of which points in the direction of the conduit element and one of which points in the direction of the hose element. It is thereby possible to establish, before surgery, the connection between the connecting element and the conduit element and to subsequently establish the connection to the hose element.

Advantageously, it can also be provided that the connecting element can be slid axially into the hose element and, in the connected state, to be located radially within the hose element.

To this end, the diameter of the hose element must be matched precisely to that of the connecting element. In addition, a pressure element that encloses both sealing partners from radially outside can be provided, said pressure element compressing the sealing partners of this radial seal. Said seal is thereby prevented from leaking, which would otherwise result in the unwanted accumulation of small quantities of blood when used in a blood vessel or of other bodily fluids, and which must be prevented to prevent decay processes or other processes of the bodily fluids, such as blood coagulation, for example, to take place there in an uncontrolled manner.

The connecting element can also be slid axially into the conduit element. To this end, the conduit element can be elastically expandable, and a pressure element that encloses the sealing partners of the radial seal can be provided at this point, for support, in order to build up radial pressure.

A further retaining element for the axial hold can be formed, advantageously, by way of a thread binding, for example. To this end, a suture can be wound around the outer sealing partner several times, even in a spiral shape, for example, in order to build up radial pressure. To this end, the outer element of the radial seal should be radially elastically deformable at least to a certain extent in order to permit the inner sealing partner to be pressed upon. Surgical suture thread can be used to advantage as the winding thread.

To this end, a wall weakening of the outer sealing partner, that is, for example, a weakening in the wall of the hose element or the conduit element, can be provided in the region of the thread binding or, more generally, the pressure element.

In order to create a reliable seal, the connecting element can also comprise radially circumferential webs on the outer side thereof, for example, which can have a sawtooth design in the longitudinal view. This design of a hose coupling, which is known per se, creates a secure connection and ensures high seal integrity. In addition, a multistage seal is produced as a result, the reliability of which is increased further by a pressure element pressing thereupon from the outside.

The outer pressure element can also be formed by the snap ring itself, for example, which then applies the radial pressure to support the seal. To this end it is advantageous for the snap ring to have a smaller inner diameter in the unloaded state than the outer diameter of the element onto which it is snapped.

Advantageously, according to a specific variant of the connection of two elements of the connection system, said two elements, for example, the flexible hose element and the connecting element, can be screwed together by way of a circumferential thread. This is advantageous in the region of the flexible hose element in particular when said hose element is designed as a graft that already forms a thread-like structure per se. Such a central threaded connection at least ensures that the arrangement is held together axially. If the snap ring is designed and positioned in such a way that it acts upon the outer partner of said threaded connection from the outside and presses it together radially, it is thereby possible to increase the hold and the static friction as well as the seal integrity of the radial seal.

Further designs and advantageous embodiments of the invention are shown in the following in a drawing with reference to an exemplary embodiment, and are subsequently described.

BRIEF DESCRIPTION OF THE DRAWINGS

Shown are

FIG. 1 a schematic depiction of three parts of a connection system, in a longitudinal view, FIG. 2 a conduit element comprising a retaining element, in the upper part with the beaded snap ring, in the lower part in the connected state, FIG. 3a a flexible hose element comprising a connecting element fixedly (non-detachably) connected thereto, FIG. 3b an enlarged part of FIG. 3a, FIG. 4 a longitudinal view of a hose element/graft, which is connected to a connecting element, before insertion into a conduit element, FIG. 5 a longitudinal view of a connection system in the joined state/connected state, FIG. 6 a connection system in which the retaining element is connected to the conduit element and the connecting element comprises a circumferential thread for connection to the hose element, and FIG. 7 the constellation from FIG. 6 shown in the connected state.

DESCRIPTION OF PREFERRED EMBODIMENTS

Figure 1:
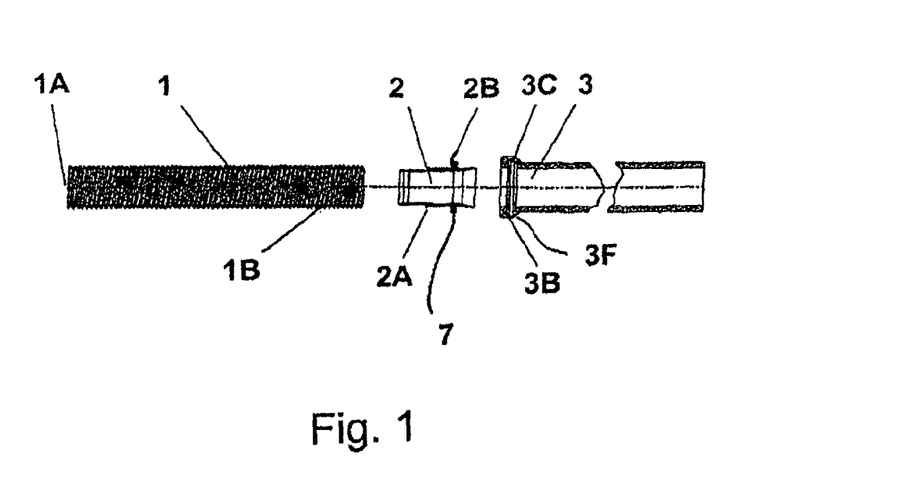

FIG. 1 shows, in a longitudinal view, one behind the other, the connection system comprising a flexible hose element 1 in the form of a graft, and a conduit element 3 in the form of a tube made of a silicone or a silicone elastomer. The connecting element 2 is also shown, which comprises an azimuthally circumferential web that forms a detent surface 2B. The three elements of the connection system are disposed axially one behind the other and coaxially with respect to one another.

The graft is made of a polyester fabric, although it can also be made of another plastic. The conduit element 3 can be made of a polyurethane instead of silicone. The connecting element 2 is advantageously made of a metal, in particular of titanium.

Advantageously, the connecting element 2 is either fixedly connected to the conduit element 3 or to the hose element 1. The fixedly connected parts are sterilized and packaged together as a fixed connection, while the part that supplements the entire connection (the hose element or the conduit element) can be sterilized and packaged separately.

The connecting element 2 is sized in such a way that the two ends thereof can be slid into the graft and into the conduit element. Typically, however, one of these connections is already prefabricated.

Of the ends 1A, 1B of the graft 1, the first end 1A is typically sutured to a blood vessel, while the second end 1B is connected to the connecting element 2.

The conduit element 3 comprises, on the end thereof facing the connecting element 2, a retaining element 3B, 3C, 3F that is folded over a web 7 extending azimuthally around the cylinder jacket surface of the connecting element 2 and is snapped in at a detent surface 2B.

Figure 2:
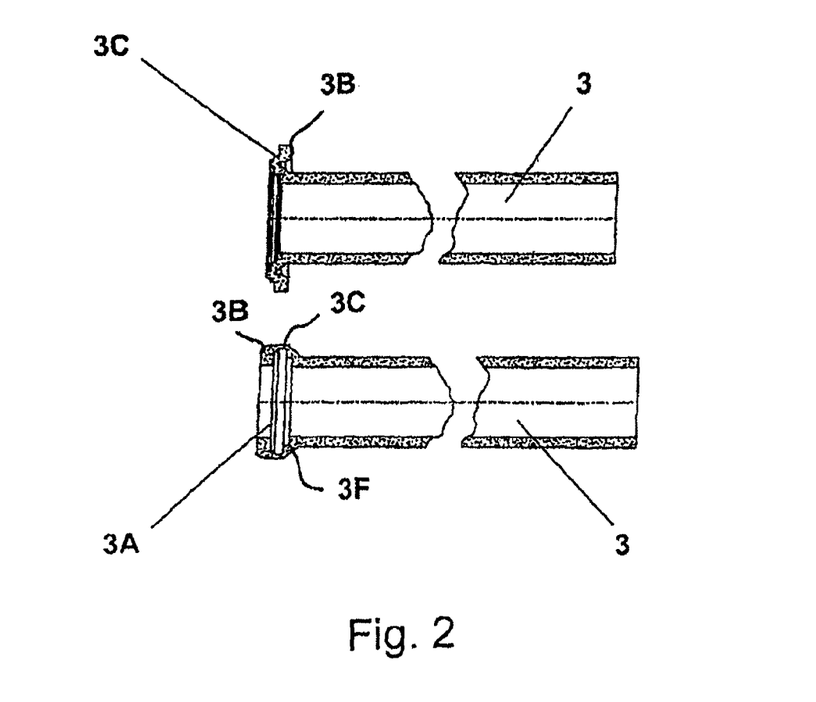

FIG. 2 shows, in the top part, the retaining element comprising a snap ring 3B that has been beaded toward the rear, while the lower part of the figure shows the retaining element in the connected state. In the connected state, the retaining element 3B, 3C, 3F protrudes axially beyond the tubular part of the conduit element 3. To this end, the retaining element comprises a conical, cylindrically circumferential region 3F of a hose connector, and a region 3C in which the hose connector extends cylindrically and with a constant inner diameter and outer diameter, and in which the hose connector is characterized by a weakened wall region. This weakened wall region is adjoined by the snap ring 3B having a greater wall thickness, wherein the thickness of the snap ring is sized such that the snap ring, in the connected state, for example, can still apply an appropriately great radial pressure effect but can still be expanded elastically just enough to permit beading of the retaining element. The diameter of the snap ring in the snapped-in state is labelled 3A in FIG. 2. The elastic expandability of the snap ring can be controlled in a suitable manner by way of the material thickness and the selection of the material and by way of indentations and recesses that may be provided. It is particularly advantageous, however, for the snap ring to be designed with a constant cross section and without indentations.

The geometry of the retaining element is advantageously designed such that it is self-stabilizing in the beaded state of the snap ring 3B, thereby making it possible to sterilize, transport and stockpile the conduit element in this state.

The inner diameter 3D of the snap ring 3B in the unloaded state can be selected to be the same size as the inner diameter of the tube part of the conduit—element 3.

Figures 3A, 3B:
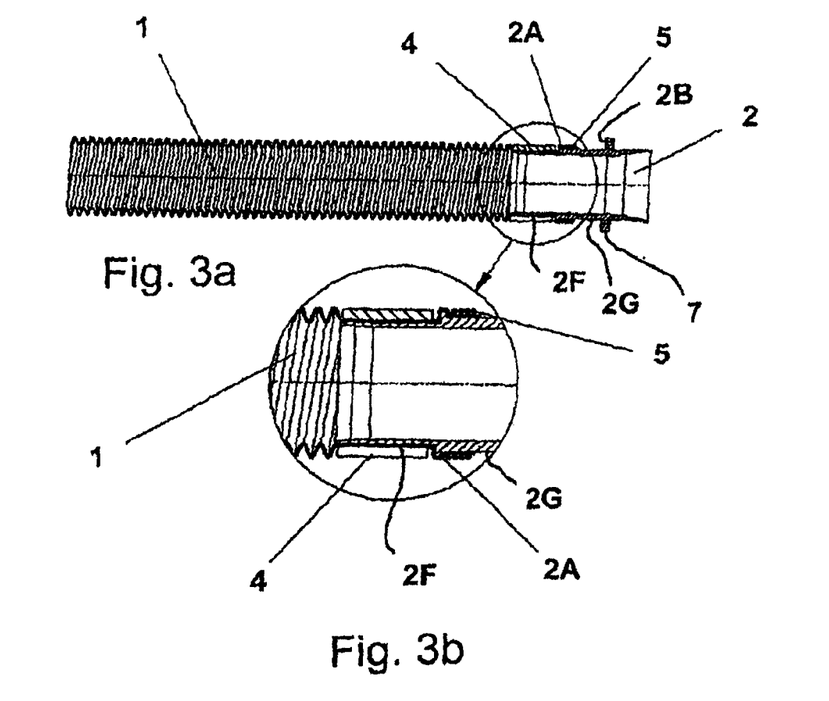

FIG. 3a shows the graft 1 in a fixed connection with a connecting element 2. The connecting element 2 comprises an end section 2F and a central section 2G, which are separated from one another by a circumferential collar or a shoulder 2A. The connecting element has a smaller outer diameter in the end section 2F than in the central section 2G.

For connection, the end 1B of the graft 1 is slotted in the region in which it is intended to be slid over the collar 2A, and is slid over the connecting element 2. Next, the slotted longitudinal region of the graft 1 is wrapped in the central section 2G with a thread binding 5 and is pressed against the central section 2G of the connecting element 2. In order to seal the part of the graft 1 lying on top in the end region 2F with respect to the connecting element 2, a slotted annular sleeve 4 is slid on at that point, which exerts radial pressure onto the graft 1, thereby preventing the radial seal between the graft and the connecting element 2 from leaking in this region and affixing the graft. The slotted ring 4 can be made of titanium, for example. An unslotted elastic ring, such as a silicone ring, can also be used at this point.

FIG. 3b shows the region of the end section 2F, the collar 2A and the central section 2G in an enlarged depiction.

Figure 4:
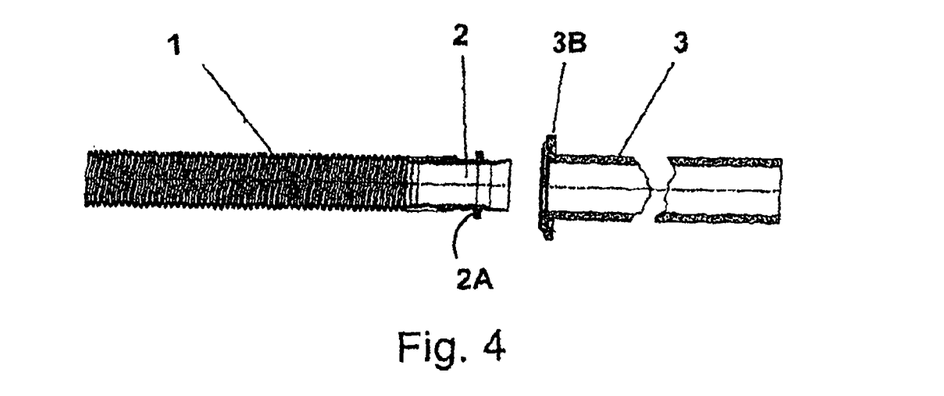

FIG. 4 shows the prefabricated connection between the graft 1 and the connecting element 2, as described according to FIGS. 3a and 3b, before joining to the conduit element 3, which is designed as a connecting cannula, and in FIG. 4 in the beaded state of the retaining element with the snap ring 3B stretched thereon.

Figure 5:
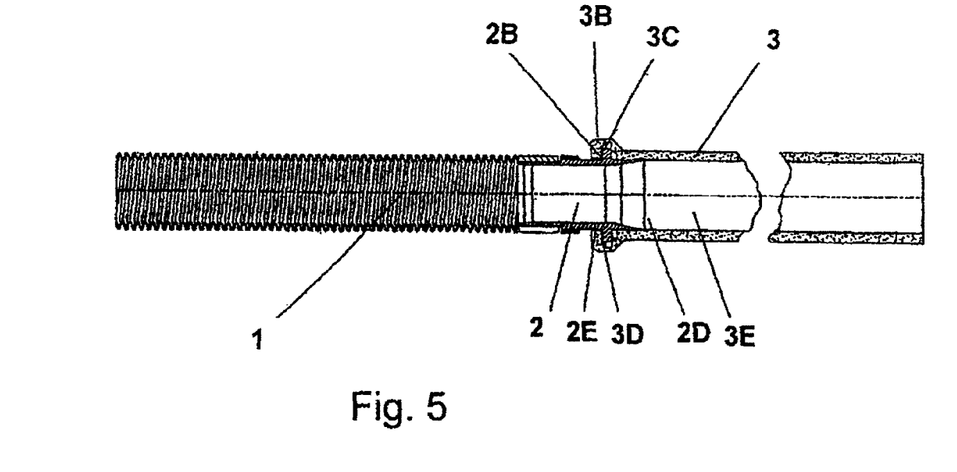

The connecting element 2 is now slid into the conduit element 3, as shown more precisely in FIG. 5, and the snap ring 3B is snapped in behind the detent surface 2A at the outwardly azimuthally circumferential web of the connecting element 2.

In the region 2E of the connecting element 2, which is shown in FIG. 5, said connecting element has an outer diameter that is greater than the inner diameter of the snap ring 3B in the unloaded state. As a result, the graft can also be pressed radially against the connecting element by way of the snap ring in this region if it extends thereto, and is therefore additionally retained. There, in addition to the radial seal of these parts in the region 2D, the conduit element 3 comprising the connecting element is sealed in an axial seal, where the connecting element can have a sawtooth-shaped structure of outer rings on an outer side thereof, for example, to permit it to be pressed there elastically against the conduit element 3. It is thereby possible to prevent fluid, more particularly blood, from entering the region of the retaining element 3B, 3C.

Figure 6:
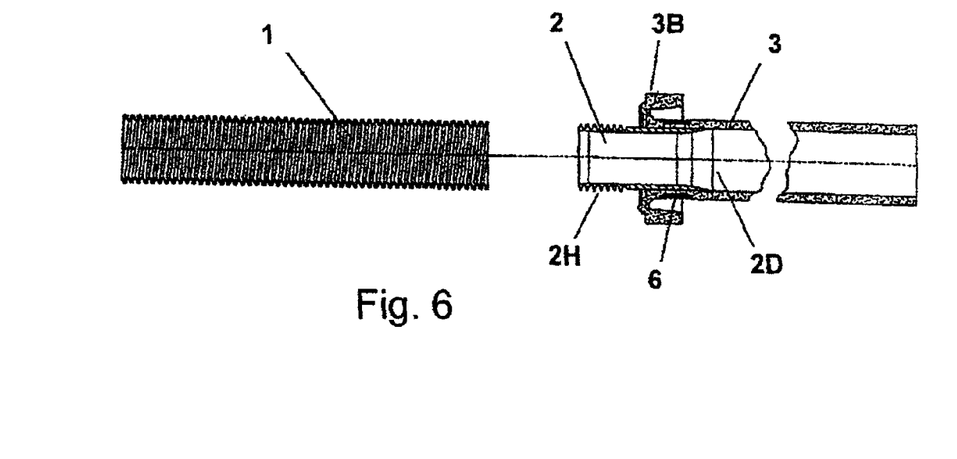

FIG. 6 shows a modified embodiment of the invention in which a weakened wall region is provided in front of the retaining element 3B, 3C on the outer side of the conduit element 3, in which a thread binding 6 can be disposed in order to radially press the conduit element 3 against the connecting element 2 there and thereby secure the hold. The radial seal between the connecting element and the conduit element is ensured by way of a circumferential edge of the connecting element, which rests against the inner side of the elastic conduit element.

In addition, an outer thread 2H is provided at the end of the connecting element 2 facing the graft, which substantially corresponds to the helical structure of the graft 1 and onto which the graft can be screwed. The seal integrity is also established here by way of radial pressure, for example by way of a pressing ring that is installed.

The seal of the connecting element with respect to the conduit element is brought about substantially by an elastic placement of the conduit element on the circumferential edge 2D of the connecting element.

Figure 7:
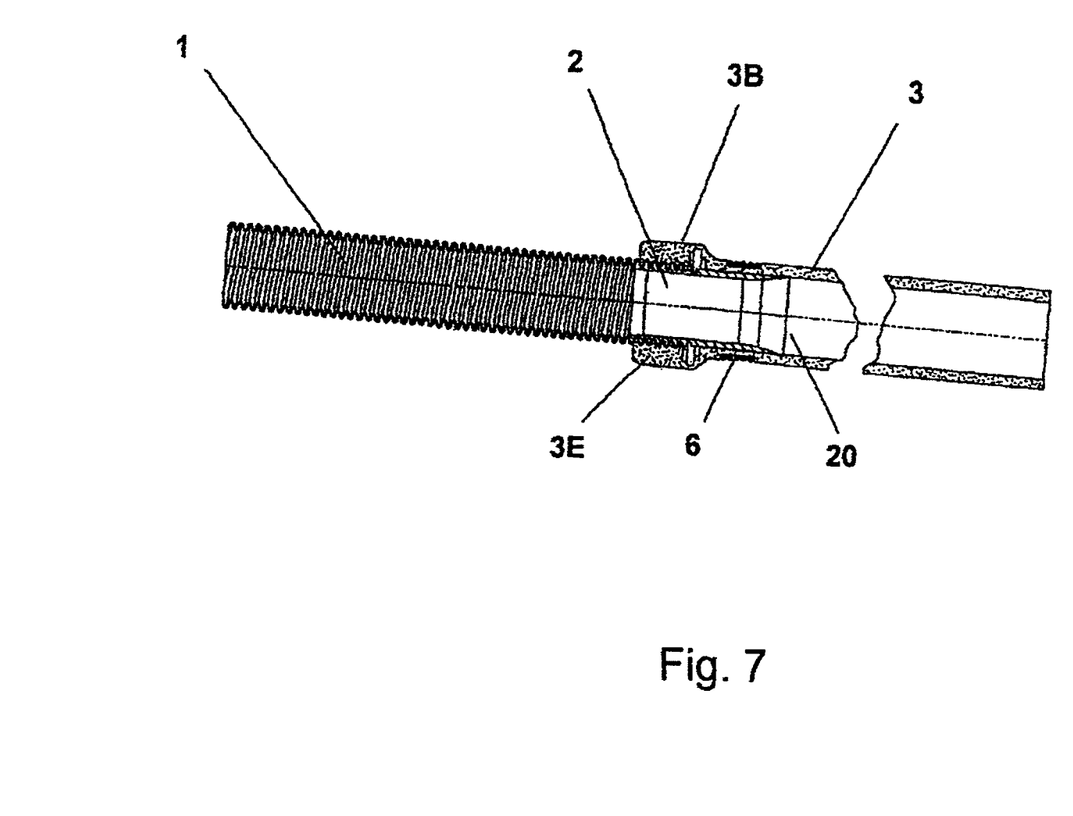

FIG. 7 shows the connected state for this case, in which the snap ring 3B, which has a relative solid design, is folded radially onto the graft in the screwed-in state, and therefore the graft is pressed radially onto the connecting element by the snap ring in an elastic manner in the region of the thread in order to refine the seal. At the same time, the elastically pressed-on snap ring 3B prevents the axial removal there of the graft from the connecting element 2 as well as rotation, which could cause the thread to become disengaged.

The invention easily makes it possible to establish a reliably tight connection of a connection system comprising three elements, wherein, advantageously, the connecting element is already prefabricated with one of the other elements, ideally with the conduit element, and therefore two parts are joined shortly before surgery. It is thereby possible to procure from various manufacturers or from various inventories and to procure a combination of various parts that are selected as needed. If one of the parts of the connection system must be replaced during surgery, the remaining parts can still be used without a problem.

The invention thereby contributes to the simplification of surgeries in which vascular cannulas must be created, wherein optimized procurement and stockpiling is also made possible.

The invention claimed is:

1. A connection system for creating a vascular cannula for connection to a blood vessel, comprising a flexible tube element, the flexible tube element being a radially non-expandable graft, a conduit element and a connecting element for fluid-tight connection to the tube element and to the conduit element, wherein the connecting element axially overlaps the tube element and the conduit element, and wherein a retaining element is equipped with a radially elastically expandable snap ring, which can be beaded radially outwardly over other parts of the retaining element, and which, in the connected state, can be snapped onto an element of the connection system;

wherein the connecting element includes a first end section and a central section separated by a shoulder, wherein the flexible tube element axially overlaps the first end section of the connecting element;

wherein the connection system comprises a pressure element which, in the connected state, presses the flexible tube element radially against the first end section of the connection element and which terminates axially at the shoulder of the connection element; and wherein the flexible tube axially overlaps the shoulder and, at least partly, the central section of the connection element, wherein an end portion of the flexible tube element axially overlapping the shoulder is slotted.

2. The connection system according to claim 1, wherein the retaining element is connected to the conduit element, more particularly being connected thereto as a single piece.

3. The connection system according to claim 1 or 2, wherein the retaining element is connected to the connecting element, more particularly being connected thereto as a single piece.

4. The connection system according to claim 1 or 2, wherein the connecting element can be slid axially into the flexible tube element and, in the connected state, is located at least partially radially within the tube element.

5. The connection system according to claim 1 or 2, wherein the connecting element can be slid axially into the conduit element and, in the connected state, is located at least partially radially within the conduit element.

6. The connection system according to claim 1 or 2, further comprising two seals between the connecting element and the conduit element and the flexible tube element that are in the form of radial seals, and wherein at least one of the seals of the connecting element with the flexible tube element and with the conduit element is compressed radially by way of the pressure element that encloses both sealing partners radially from the outside.

7. The connection system according to claim 6, wherein a second pressure element is formed by a thread binding.

8. The connection system according to claim 1 or 2, wherein the snap ring, in the connected state, applies a radial force onto the element onto which it is snapped.

9. The connection system according to claim 1 or 2, wherein the snap ring, in the unloaded state, has an inner diameter that is smaller than the outer diameter of the element onto which it can be snapped.

10. The connection system according to claim 1 or 2, wherein the element of the connection system onto which the snap ring can be snapped comprises an outwardly azimuthally circumferential detent surface, behind which the snap ring snaps in, and/or a circumferential thread for screwing on a further element of the connection system.

11. The connection system according to claim 1, further comprising two seals between the connecting element and the conduit element and between the connecting element and the flexible tube element, respectively, wherein the two seals are in the form of radial seals, and wherein one of the two seals of the connecting element is compressed radially by way of the pressure element.

12. The connection system according to claim 1, wherein the connecting element has a smaller outer diameter in the first end section than in the central section.

13. The connection system according to claim 1, wherein the connection element includes a second end section which is separated from the central section of the connection element by the element of the connection system onto which the snap ring can be snapped, wherein the conduit element axially overlaps the second end section of the connection element.

14. The connection system according to claim 1, wherein the conduit element comprises silicon and/or silicone elastomer.

15. A connection system for creating a vascular cannula for connection to a blood vessel, comprising a flexible tube element, more particularly a graft, a conduit element and a connecting element for fluid-tight connection to the tube element and to the conduit element, wherein the connecting element axially overlaps the tube element and the conduit element, the connection system comprising a retaining element including a flange, a tube piece and a snap ring, the flange extending around the conduit element on the outside, the tube piece being fastened to the flange, extending coaxially with respect to the conduit element and terminating in the snap ring, wherein the snap ring can be elastically widened and folded axially backwards behind the tube piece and, in the connected state, can be snapped onto an element of the connection system;
- wherein the connection system comprises a sleeve which, in the connected state, presses the flexible tube element radially against a first end section of the connection element and which terminates axially at a shoulder of the connection element; and
- wherein the flexible tube axially overlaps the shoulder and, at least partly, a central section of the connection element, wherein an end portion of the flexible tube element axially overlapping the shoulder is slotted.

16. The connection system according to claim 15, wherein the tube piece comprises at least one weakening region in which a wall thereof is weakened in an azimuthal circumferential manner.

17. The connection system according to claim 16, wherein the retaining element, in its folded configuration, is self-stabilizing.

18. The connection system according to claim 15, wherein the retaining element is formed integrally with the conduit element, the retaining element being formed of the same elastic material as the conduit element.

\* \* \* \* \*